US00PP15197P2

(12) United States Plant Patent
Olesen et al.

(10) Patent No.: US PP15,197 P2
(45) Date of Patent: Sep. 28, 2004

(54) ROSE PLANT NAMED 'POULEN007'

(50) Latin Name: *Rosa hybrida*
Varietal Denomination: POULen007

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,149

(22) Filed: Dec. 16, 2003

(51) Int. Cl.[7] ..... A01H 5/00
(52) U.S. Cl. ..... Plt./140
(58) Field of Search ..... Plt./140

*Primary Examiner*—Anne Marie Grunberg
*Assistant Examiner*—Annette H Para

(57) ABSTRACT

A new garden rose plant of the hybrid tea class which has abundant dark red flowers, exceptional fragrance, and attractive foliage. This new and distinct variety has shown to be uniform and stable in the resulting generations from asexual propagation.

2 Drawing Sheets

Botanical classification: *Rosa hybrida.*
Variety denomination: 'POULen007'.

SUMMARY OF THE INVENTION

The present invention constitutes a new and distinct variety of garden rose plant which originated from a controlled crossing between the female parent, an unnamed seedling, and the male parent, 'POULskov', described and illustrated in U.S. Plant Pat. No. 9,062 dated Feb. 28, 1995. The two parents were crossed during the summer of 1995 and the resulting seeds were planted in a controlled environment in Fredensborg, Denmark. The new variety is named 'POULen007'.

The new variety may be distinguished from its seed parent, by the following combination of characteristics:

1. The seed parent has 40 petals. 'POULen007' has 40 to 50 petals.
2. The seed parent has a soft pink flower. 'POULen007' has a dark red flower.

The new variety may be distinguished from its pollen parent, 'POULskov' by the following combination of characteristics:

1. The pollen parent has a flower diameter of 15 cm. 'POUULen007' has a flower diameter between 8 to 10 cm.
2. The pollen parent has a petal count of 60 petals. 'POULen007' has a petal count of 40 to 50 petals.
3. The general tonality of the pollen parent is Red Group 54A. 'POULen007' is Red-Purple Group 61A.

The objective of the hybridization of this rose variety was to create a new and distinct variety for garden use with unique qualities, such as:

1. Uniform and abundant dark red flowers;
2. Vigorous, but compact growth when propagated both as a budded rose and on its own roots;
3. Disease resistance;
4. Exceptional fragrance.

This combination of qualities is not present in previously available commercial cultivars of this type, known to the inventors, and distinguish 'POULen007' from all other varieties of which we are aware.

As part of their rose development program, L. Pernille Olesen and Mogens N. Olesen germinated the seeds from the aforementioned hybridization during winter 1995 and conducted evaluations on the resulting seedlings in a controlled environment in Fredensborg, Denmark.

'POULen007' was selected in the spring 1996 by the inventors as a single plant from the progeny of the aforementioned hybridization.

Asexual reproduction of 'POULen007' by traditional budding and rooted cuttings was first done by L. Pernille and Mogens N. Olesen in their nursery in Fredensborg, Denmark in July, 1996. This initial and other subsequent asexual propagations conducted in controlled environments have demonstrated that the characteristics of 'POULen007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen007'. Specifically illustrated in SHEET 1:

FIG. 1.2; Flower bud closed, flower bud as sepals unfold, and partially open;

Specifically illustrated in SHEET 2:

FIG. 2.1; Juvenile leaf;

FIG. 2.2; Sepals, receptacle, and peduncle;

FIG. 2.3; Flower petals, detached;

FIG. 2.4; Mature leaf and bare stem exhibiting thorns and anthocyanin.

DETAILED DESCRIPTION OF THE VARIETY

Figures 1A, 1B:
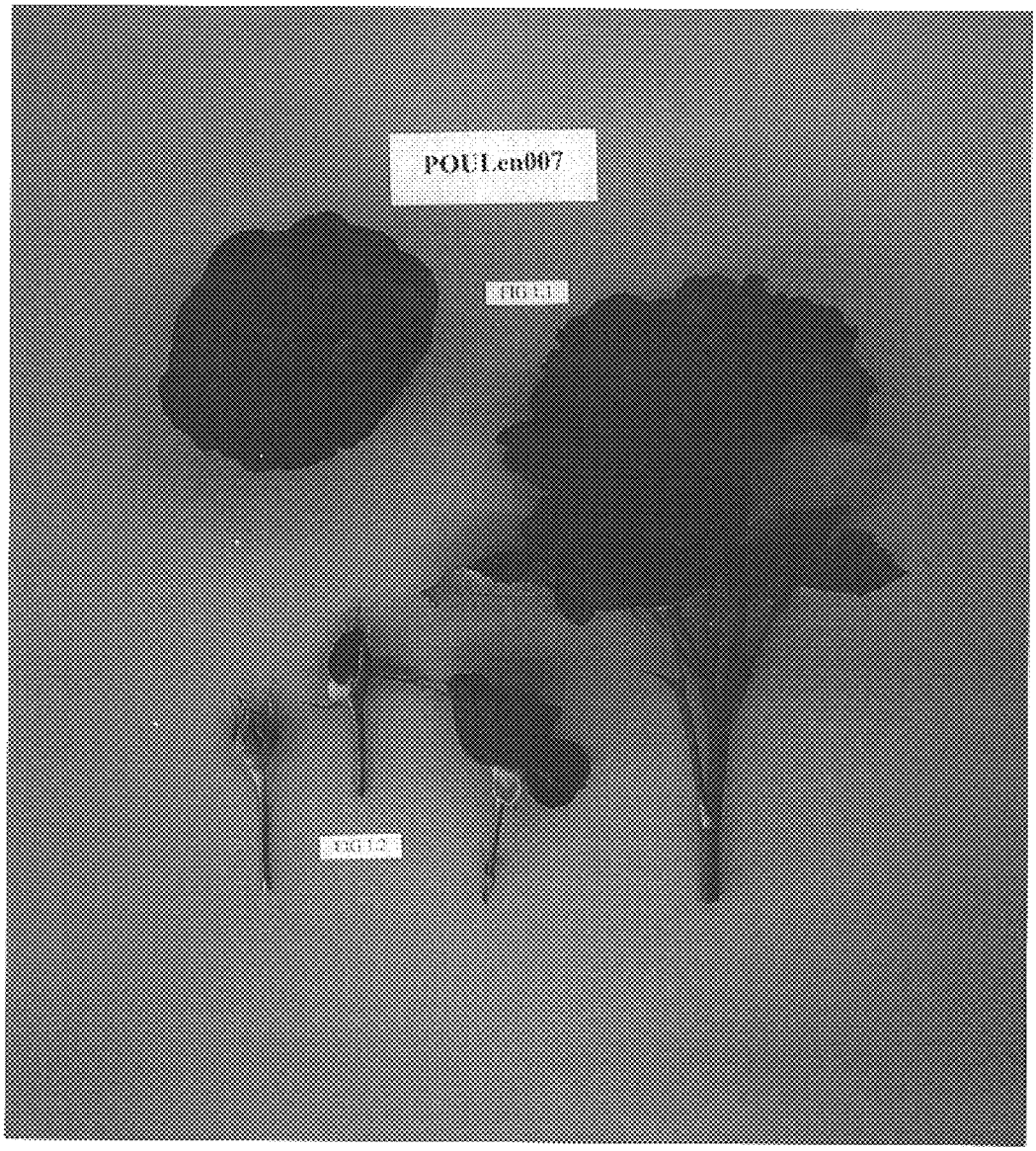
FIG. 1.1; Open flower, stem showing cluster of open flower, branching, and the attachment of leaves, buds, and peduncles.

The following is a description of 'POULen007', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULisab', a rose variety from the same inventors described and illustrated in U.S. Plant Pat. No. 12,825 dated Aug. 6, 2002 are compared to 'POULen007' in Chart 1.

CHART 1

| | 'POULen007' | 'POULisab' |
|---|---|---|
| Flower Color | Red-Purple Group 61A. | Red Group Group 46A. |
| Petalage | 55 to 60 petals. | 55 to 70 petals. |
| Color of petals | Red-Purple Group 61A. | Red Group 53A to 53B. |

FLOWER AND FLOWER BUD

Blooming habit: Recurrent.

Flower bud:

*Size.*—Upon opening, 25 mm in length from base of receptacle to end of bud.

*Bud form.*—Broad Based and ovoid.

*Bud color.*—As sepals unfold, petals are Red-Purple Group 61A. At ¼ opening petals are Red-Purple Group 61A.

*Sepals.*—Upper Surface: Color: Greyed-Purple Group 184A. Texture: Smooth and moderately pubescent. Lower Surface: Color: Greyed-Purple Group 185A. Texture: Smooth and no stipitate. Shape: Sepal apex is cirrose. Base is flat at union with receptacle. Margins: Medium to weak foliaceous appendages on three of the five sepals. Size: 36 mm (l)×12 mm (w).

*Receptacle.*—Surface: Smooth and glabrous. Shape: Urn-shaped. Size: 12 mm (h)×9 mm (w). Color: Yellow-Green Group 144B with anthocyanic intonations of Greyed-Red Group 181B.

*Peduncle.*—Surface: Glabrous. Length: 40 mm to 50 mm. Color: Yellow-Green Group 144B. Anthocyanin: Greyed-Red Group 181B. Strength: Strong.

*Borne.*—Multiple of 6 buds per flowering stem.

Flower bloom:

*Fragrance.*—Very strong rose perfume like scent.

*Duration.*—The blooms have a duration on the plant of approximately 10 days. Afterwards, petals fall cleanly away from plant.

*Size.*—Average flower diameter is 90 mm when open.

*Form.*—General shape is a cupped rosette with numerous petals packed into quarter sections.

*Shape of flower when viewed from the side.*—Upon opening: The upper and lower parts are flat. Open flower: The upper part is flat. The lower part is convex.

*Petalage.*—Average range: 68 to 73 petals under normal conditions with 13 petaloids.

*Color.*—

*Upon opening, petals.*—Outermost petals: Outer side: Red-Purple Group 61A. Inner Side: Red-Purple Group 61A. Innermost petals: Outer side: Red-Purple Group 61A. Inner Side: Red-Purple Group 61A.

*Upon opening, basal petal spots.*—Outermost petals: Outer side: Yellow-White Group 158D. Inner Side: Yellow-White Group 158D. Innermost petals: Outer side: Yellow-White Group 158D. Inner Side: Yellow-White Group 158D.

*After opening, petals.*—Outermost petals: Outer side: Red-Purple Group 61A. Inner Side: Red-Purple Group 61A. Innermost petals: Outer side: Red-Purple Group 61A. Inner Side: Red-Purple Group 61A.

*After opening, basal petal spots.*—Outermost petals: Outer Side: Yellow-White Group 158D. Inner Side: Yellow-White Group 158D. Innermost petals: Outer Side: Yellow-White Group 158D. Inner Side: Yellow-White Group 158D.

General tonality: On an open flower, Red-Purple Group 61A. No change in the general tonality at the end of the 10th day.

*Petals.*—Petal Reflex: Petals reflex slightly. Margin: Entire and uniform with medium undulations of margin. Shape: Apex: Round. Base: Rounded. Size: 50 mm (l)×50 mm (w). Thickness: Average to thin. Arrangement: Not Formal.

*Petaloids.*— Quantity: 13 to 15 in number. Color: Red-Purple Group 61A. Size: 25 mm (l)×25 mm (w).

*Reproductive Organs.*—Pistils: Length: 9 mm. Quantity: 62. Pollen: Color: Greyed-yellow Group 161B. Quantity: Scant. Anthers: Size: 3 mm. Color: Greyed-Yellow Group 161B. Quantity: 98 (actual count). Filaments: Color: White Group 155A with weak intonations of Violet Group 48B. Length: 7 mm. Stigmas: Superior relative to the height and length of the anthers. Color: Greyed-Yellow Group 161A. Styles: Color: Yellow-Green Group 150D. Other Intonations: Red Group 50B. Hips: None Observed in the field nursery in Jackson County Oreg.

PLANT

Plant growth: Moderate, upright to bushy. When grown as a budded field grown plant on *Rosa multiflora* understock, the average height of the plant is 100 to 150 cm. The average width is 100 cm.

Stems:

*Color.*—Young wood: Yellow-Green Group 144B. Older wood: Yellow-Green Group 144B. Anthocyanin: Location: Observed on old and new growth. Color: Greyed-Red Group 181B.

*Surface Texture.*—Young wood: Smooth. Older wood: Smooth.

*Thorns.*—Incidence: 5 thorns per 10 cm of stem. Size: 5 mm average. Color: Greyed-Purple Group 183A. Shape: Deeply concave to concave.

Plant foliage: Normal number of leaflets on normal leaves in middle of the stem: 5 leaflets.

*Compound Leaf size.*—120 mm (l)×90 mm (w).

*Quantity.*—Average.

*Color.*—Mature Foliage: Upper Leaf Surface: Yellow-Green Group 146A. Lower Leaf Surface: Yellow-Green Group 146C to 146D. Juvenile foliage: Upper Leaf Surface: Yellow-Green Group 146B. Lower Leaf Surface: Yellow-Green Group 147C. Anthocyanin: Location: Margins of juvenile foliage. Color: Greyed-Purple Group 187A.

Plant leaves and leaflets:

*Stipules.*—Size: 23 mm in length. Color: Yellow-Green Group 146A. Margins: Stipitate glands observed. Anthocyanin: Color: Greyed-Purple Group 185A.

*Petiole.*—Length: 35 mm. Color: Yellow-Green Group 144B. Underneath: Smooth and glabrous. Margins: Stipitate glands present. Anthocyanin: Greyed-Purple Group 183B.

*Rachis.*—Size: 40 mm. Color: Yellow-Green Group 144B. Underneath: Smooth and glabrous. Margins: Stipitate glands present. Anthocyanin: Greyed-Purple Group 183B.

*Leaflet.*—Size: 45 to 55 mm (l)×30 to 40 mm (w). Edge: Doubly serrated. Shape: Generally ovate. Apex is Cuspidate. Base is Round. Texture: Smooth. Arrangement: Odd pinnate. Venation: Reticulate. Glossiness: Moderately glossy. Thickness: Medium to thick.

Disease resistance: Above average resistance to mildew, rust, black spot, and Botrytis under normal growing conditions in Jackson County, Oreg.

Cold Hardiness: The variety 'POULen007' has been found to be cold tolerant to USDA Cold Hardiness Zone 6.

We claim:

1. A new and distinct variety of rose plant of the hybrid tea rose class, substantially as herein illustrated and described as a distinct and novel rose variety due to its abundant dark red flowers, strong fragrance, disease resistance, and extended period of bloom.

* * * * *

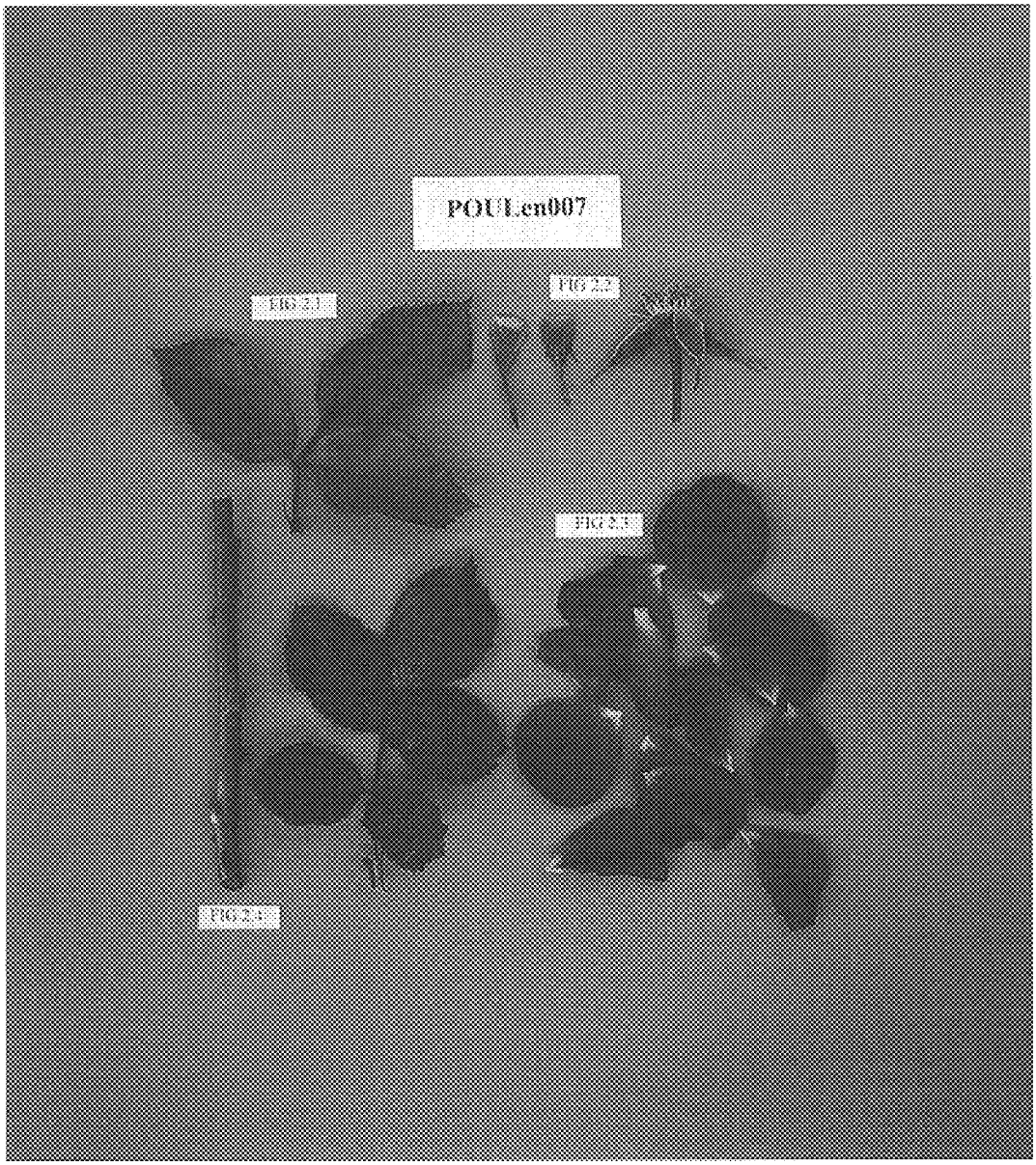
POULen007
FIG 2.1
FIG 2.2
FIG 2.3
FIG 2.4